(12) United States Patent
Germain et al.

(10) Patent No.: US 12,076,076 B2
(45) Date of Patent: Sep. 3, 2024

(54) ARTHROSCOPIC DEVICES AND METHODS

(71) Applicant: RELIGN Corporation, Campbell, CA (US)

(72) Inventors: Aaron Germain, San Jose, CA (US); Jeff Norton, Emerald Hills, CA (US)

(73) Assignee: Relign Corporation, Campbell, CA (US)

( * ) Notice: Subject to any disclaimer, the term of this patent is extended or adjusted under 35 U.S.C. 154(b) by 903 days.

(21) Appl. No.: 16/919,480

(22) Filed: Jul. 2, 2020

(65) Prior Publication Data

US 2021/0007793 A1 Jan. 14, 2021

Related U.S. Application Data

(60) Provisional application No. 62/872,134, filed on Jul. 9, 2019.

(51) Int. Cl.
*A61B 18/14* (2006.01)
*A61B 17/32* (2006.01)
(Continued)

(52) U.S. Cl.
CPC ........ *A61B 18/148* (2013.01); *A61B 18/1206* (2013.01); *A61B 17/320016* (2013.01); *A61B 17/32002* (2013.01); *A61B 17/320036* (2013.01); *A61B 2018/00208* (2013.01); *A61B 2018/00565* (2013.01); *A61B 2018/00577* (2013.01); *A61B 2018/00595* (2013.01); *A61B 2018/00607* (2013.01); *A61B 2018/00916* (2013.01); *A61B 2018/00982* (2013.01); *A61B 2018/126* (2013.01); *A61B 18/149* (2013.01); *A61B 2218/007* (2013.01)

(58) Field of Classification Search
CPC ...... A61B 17/320016; A61B 17/32002; A61B 17/320036; A61B 2017/320024; A61B 2017/320028; A61B 2017/320032; A61B 2017/32004; A61B 2018/00202; A61B 2018/00208; A61B 2018/00565; A61B 2018/00577; A61B 2018/00589; A61B 2018/00595; A61B 2018/00601; A61B 2018/00607; A61B 2018/00982; A61B 18/148; A61B 18/149; A61B 2218/007
See application file for complete search history.

(56) References Cited

U.S. PATENT DOCUMENTS 10,022,140 B2 7/2018 Germain et al.
2004/0010249 A1 1/2004 Truckai et al.
(Continued)

*Primary Examiner* — Ronald Hupczey, Jr.
*Assistant Examiner* — Bradford C. Blaise
(74) *Attorney, Agent, or Firm* — SCHWEGMAN LUNDBERG & WOESSNER, P.A.

(57) ABSTRACT

A probe for treating shoulders and other joints has a working end which includes a first element for cutting soft tissue, a second element for applying RF energy to tissue, and a third element for cutting or burring bone. The probe is introduced to a working space in a patient's joint, such as the patient's subacromial space, typically under endoscopic viewing. Soft tissue is cut with the first element. Radiofrequency energy is applied with the second element to ablate or cauterize tissue, while bone may be burred with the third element. Successive treatments steps are performed by reorienting the treatment device in situ with removal or withdrawal of the working end.

27 Claims, 8 Drawing Sheets

(51) Int. Cl.
   *A61B 18/00*   (2006.01)
   *A61B 18/12*   (2006.01)

(56) References Cited

U.S. PATENT DOCUMENTS

| | | | |
|---|---|---|---|
| 2005/0228372 A1 | 10/2005 | Truckai et al. | |
| 2007/0213704 A1 | 9/2007 | Truckai et al. | |
| 2008/0097425 A1 | 4/2008 | Truckai | |
| 2012/0029545 A1* | 2/2012 | Nelson | A61B 17/1659 |
| | | | 606/171 |
| 2012/0046682 A1* | 2/2012 | Nelson | A61B 17/1624 |
| | | | 606/180 |
| 2016/0235469 A1* | 8/2016 | Prisco | A61B 18/1485 |
| 2016/0346036 A1 | 12/2016 | Orczy-Timko et al. | |
| 2017/0100158 A1* | 4/2017 | Ueda | A61B 17/320016 |
| 2017/0128083 A1 | 5/2017 | Germain et al. | |
| 2017/0135741 A1 | 5/2017 | Germain et al. | |
| 2017/0172648 A1 | 6/2017 | Germain et al. | |
| 2017/0202612 A1 | 7/2017 | Germain et al. | |
| 2017/0224368 A1 | 8/2017 | Germain et al. | |
| 2017/0252099 A1 | 9/2017 | Orczy-Timko et al. | |
| 2017/0258519 A1 | 9/2017 | Germain et al. | |
| 2017/0290602 A1 | 10/2017 | Germain et al. | |
| 2017/0303990 A1* | 10/2017 | Benamou | A61B 17/32002 |
| 2018/0000534 A1 | 1/2018 | Germain et al. | |
| 2018/0078279 A1 | 3/2018 | Germain et al. | |
| 2018/0093391 A1 | 4/2018 | Germain et al. | |
| 2018/0161088 A1 | 6/2018 | Poser et al. | |
| 2018/0263649 A1 | 9/2018 | Germain et al. | |
| 2018/0303509 A1 | 10/2018 | Germain et al. | |
| 2018/0317957 A1 | 11/2018 | Germain et al. | |
| 2019/0008538 A1 | 1/2019 | Germain et al. | |
| 2019/0015151 A1 | 1/2019 | Germain et al. | |
| 2019/0021788 A1 | 1/2019 | Germain et al. | |
| 2019/0038305 A1* | 2/2019 | Smith | A61B 90/39 |
| 2019/0059983 A1 | 2/2019 | Germain et al. | |
| 2019/0133640 A1* | 5/2019 | Charvet | A61B 17/42 |
| 2019/0343553 A1* | 11/2019 | Worrel | A61B 17/3421 |

* cited by examiner

ARTHROSCOPIC DEVICES AND METHODS

CROSS-REFERENCE TO RELATED APPLICATIONS

This application claims the benefit of U.S. Provisional No. 62/872,134, filed Jul. 9, 2019, the entire content of which is incorporated herein by reference.

BACKGROUND OF THE INVENTION

1. Field of the Invention

This invention relates to a medical system that includes variations of motor-driven tubular cutter or arthroscopic shavers that are configured for both mechanical cutting and electrosurgical cutting, ablation and coagulation procedures.

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, endoscopic tool systems may include a reusable hand piece and a selection of interchangeable tool probes having different treatment tools or surfaces in working ends have been proposed. Such working ends may each have multiple functionalities, such as soft tissue resection, soft tissue RF ablation and hard tissue cutting, so such tools systems can provide dozens of specific functionalities, providing great flexibility.

While a significant advantage, the need for one tool system to accommodate such flexibility is a challenge. In particular, it is necessary that the hand piece and control unit for the system be provided with correct orientation of the tool probe attached to the motor driven hand piece as well as the operational parameters of the tool probe during use.

It is therefore an object of the present invention to provide improved surgical systems and methods for their use, such as improved arthroscopic tissue cutting and removal system wherein a electrosurgical device is provided with three or more tissue-modifying effectors for cutting, cauterizing, and removing bone or soft tissue from a joint or other site. It is a further object invention to provide improved systems and methods for subacromial decompression and other similar procedures. At least some of these objectives will be met by the inventions described herein.

2. Listing of Background Art

Relevant commonly-owned patent publications include: U.S. Patent Publ. Nos. US20180093391; US20180263649; US20190008538; US20180078279; US20180303509; US20170172648; US20170224368; US20170128083; US20180317957; US20190015151; US20190059983; US20180000534; US20170252099; US20180161088; US20170202612; US20160346036; US20170290602; US20190021788; US20170135741; US20170258519; US20050228372; US20070213704; US20080097425; and US20040010249, the full disclosures of which are incorporated herein by reference.

SUMMARY OF THE INVENTION

In a first aspect, the present invention provides a method for performing shoulder arthroscopy comprising forming a first and a second portal in a patient's shoulder to access the patient's subacromial space. An endoscope is introduced through the first portal to visualize the subacromial space, and a working end of a probe is introduced through the second portal into the subacromial space, where the working end includes a plurality of end effectors, typically a first element for cutting soft tissue, a second element for applying RF energy to tissue, and a third element for bone cutting or burring. The physician can use the first element, such as a cutting window, to cut soft tissue, the second element to ablate or cauterize tissue, and the third element to cut or burr hard tissue, such as bone to access targeted bone to thereby provide a complete treatment of the subacromial space.

In exemplary aspects of this method for performing shoulder arthroscopy, at least two of (i) the cutting, (ii) the applying RF energy, and (iii) the burring steps are performed successively without removing the working end of the probe from the second portal. Often all three of (i) the cutting, (ii) the applying RF energy, and (iii) the burring steps are performed successively without removing the working end of the probe from the second portal.

In further exemplary aspects of this method for performing shoulder arthroscopy, the first element comprises a windowed cutter and cutting comprises rotating the windowed cutter with a motor in a hand piece attached to the probe. When using such a windowed cutter, a negative pressure may be applied to an extraction channel which aspirates tissue cut by the windowed cutter. The second element typically comprises a RF electrode, wherein the RF electrode may be engaged against target tissue as RF energy is applied through the RF electrode. For example, the RF electrode may comprise a bi-polar electrode arrangement in the working end of the probe. Still further, the burring element typically comprises a burr-edged portion of the working end, where the burr-edged portion of the working end may be rotated with a motor in a hand piece attached to the probe. Such a burr-edged portion is typically distal to the windowed cutting portion.

The methods of shoulder arthroscopy of the present invention may still further comprise introducing a fluid into the subacromial space, where the fluid is typically electrically conductive but may be electrically non-conductive, depending on the type of procedure, and where the fluid may be aspirated to help remove cutting debris.

In a second aspect, the present invention provides a method for performing shoulder arthroscopy. Such methods typically comprise providing an arthroscopic probe having a working end configured with a first element for cutting soft tissue, a second element for applying RF energy to tissue, and a third element for bone cutting or burring The working end of the probe may be introduced into the subacromial space, and tissue may be removed from the subacromial space by successively performing each of the following steps in any order: (i) cutting soft tissue with the first element, (ii) applying RF energy to tissue with the second element and (iii) cutting and burring bone with the third element. These steps are typically performed without withdrawing the working end from the subacromial space between at least some of the successive steps.

In one example of the method, the first and second elements are disposed on the same side of the working end so that the cutting and applying RF steps with respect to some tissue may be performed without the physician changing grip on the hand piece of the probe or otherwise rotating the hand piece 180° as would be the case if the first and second elements were on opposing sides of the working end.

In specific instances, the soft tissue may include bursa. In other instances, The RF energy applying step is performed under conditions selected to ablate tissue around a bone surface and in the sub acromial space targeted for bone cutting and burring. For example, the RF energy applying step may be performed to treat a coracoacromial ligament. Alternatively, RF energy applying step may be performed to coagulate blood vessels. In other instances, the cutting and burring bone step may be performed to remove bone from the acromion.

In other instances, the methods herein may further comprise visualizing the subacromial space with an endoscope while performing the removing step, introducing a fluid into the subacromial space, or other adjunct protocols.

In a third aspect, the present invention provides method of arthroscopic treatment comprising providing an arthroscopic probe having a working end configured with a first element for cutting soft tissue, a second element for applying RF energy to tissue and a third element for bone cutting or burring. The working end of the probe is introduced into a site in a patient's joint, and the joint is treated by performing each of the following steps in any order (i) cutting soft tissue with the first element, (ii) applying RF energy to ablate tissue with the second element and (iii) burring or cutting bone with the third element, typically without withdrawing the working end from the site in the patient's joint between at least some of the successive steps.

In exemplary aspects of this method, the step of cutting soft tissue includes rotating a windowed cutting member in an outer sleeve window, where said outer sleeve window has a distal barb edge for capturing and retaining tissue within said window. The site is typically in a patient's shoulder, and the arthroscopic treatment may comprise, for example, a subacromial decompression procedure. Alternatively, the site may be in a patient's knee. And the treatment may comprise a ligament repair procedure. Further alternatively, the site may be in a patient's hip, and the treatment may comprise a femoroacetabular impingement procedure.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to arthroscopic methods for removing bone and soft tissue in shoulders, knees and other joints. Variations of the invention will be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable hand piece that carries a motor drive component. This description of the general principles of this invention is not meant to limit the inventive concepts in the appended claims.

Figure 1:
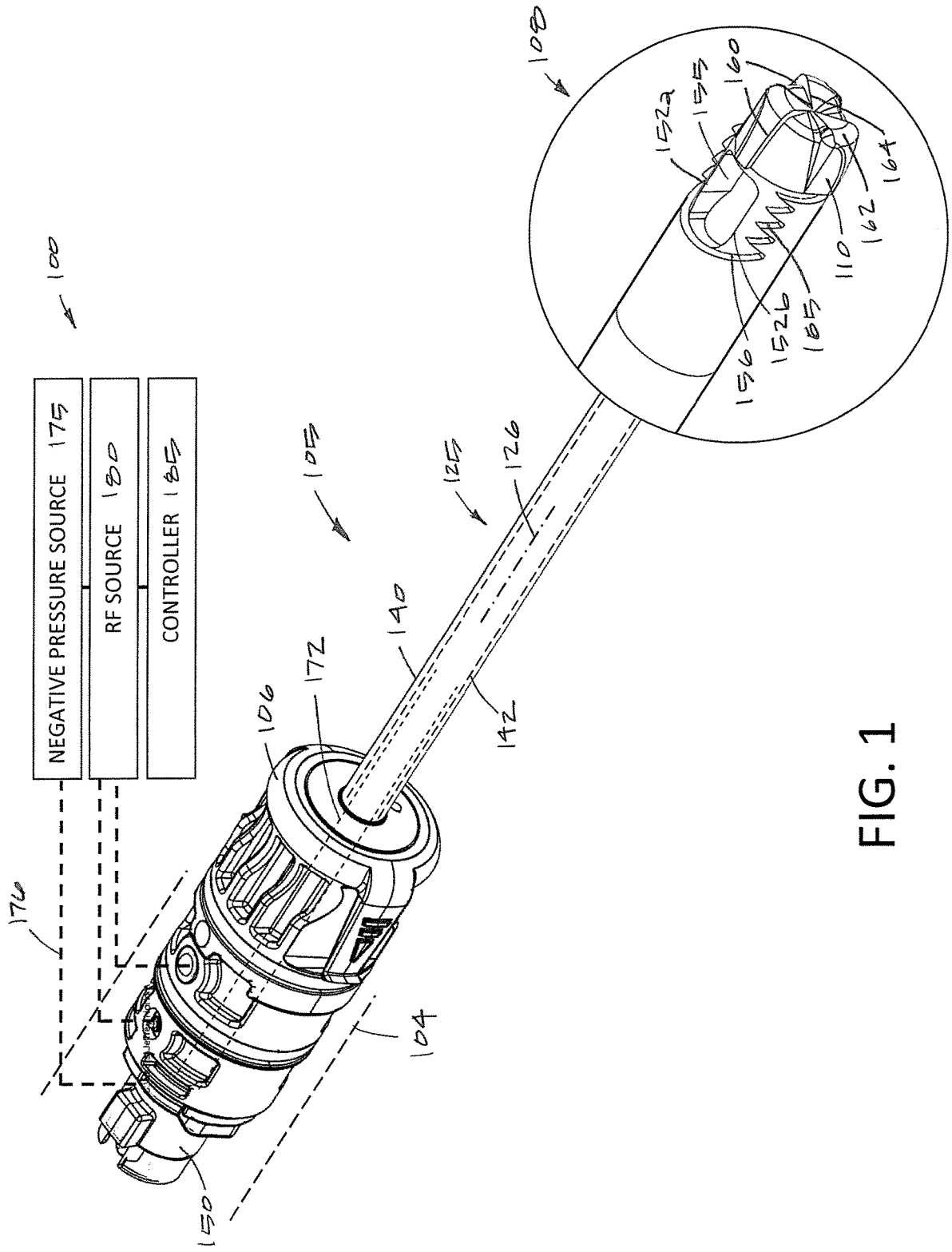
FIG. 1 is a perspective view of an arthroscopic cutting system that includes single-use cutting probe adapted for detachable coupling to a reusable hand piece with a motor drive.

In one variation shown in FIG. 1, the arthroscopic system 100 of the present invention provides a hand piece 104 (phantom view) with a motor drive and a disposable shaver assembly or probe 105 with a proximal hub 106 that can be received by receiver or bore in the hand piece 104. A hand piece 104 and probe similar to the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

In one aspect, the probe 105 has a working end 108 that carries a high-speed rotating ceramic cutter 110 that is configured for use in many arthroscopic surgical applications, including but not limited to treating bone in shoulders, knees, hips, wrists, ankles and the spine. The working end 108 further includes an active electrode 115 (FIG. 2B) and return electrode 120 further describe below.

Figure 2A:
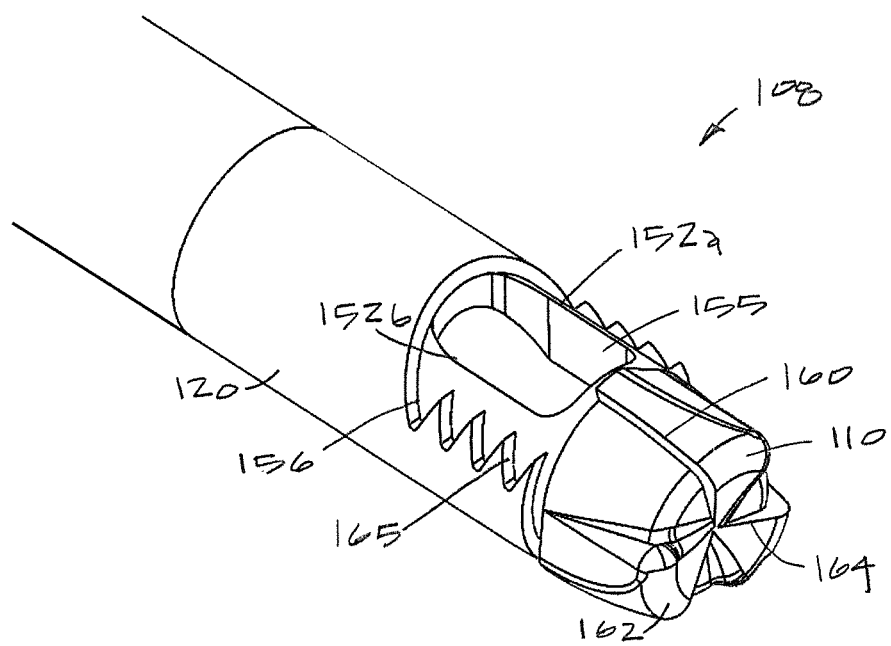
FIG. 2A is an enlarged perspective view of the probe of FIG. 1 showing the working end with the inner rotatable cutting member and cutting window in a first position relative to the outer sleeve window.
Figure 2B:
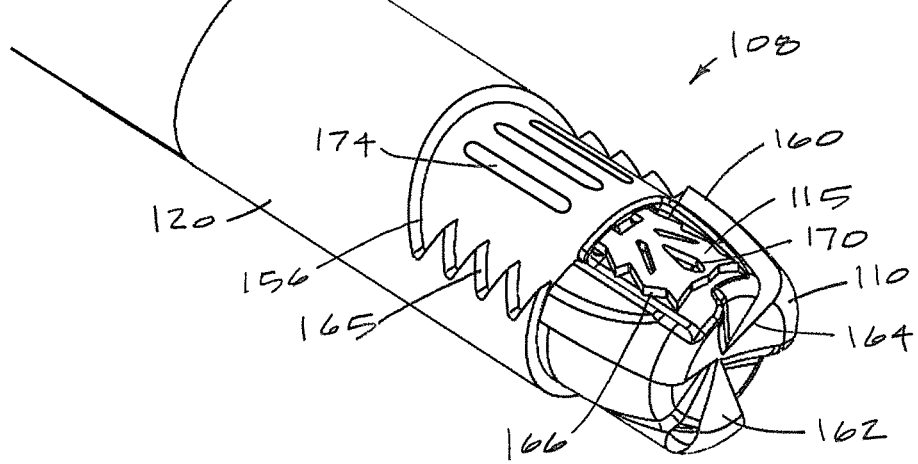
FIG. 2B is a perspective view of the working end of FIG. 2A with the inner rotatable cutting member rotated 180° so that the active electrode carried by the rotatable cutting member is in a second position relative to the outer sleeve window.

In FIGS. 1, 2A and 2B, it can be seen that probe 105 has a shaft 125 extending along longitudinal axis 126 that comprises an outer sleeve 140 and an inner sleeve 142 rotatably disposed therein with the inner sleeve 142 carrying the distal ceramic cutting member 110 (see FIGS. 1, 2A-2B). The shaft 125 extends from the proximal hub 106 wherein the outer sleeve 140 is coupled in a fixed manner to the hub 106 which can be an injection molded plastic, for example, with the outer sleeve 140 insert molded therein. The inner sleeve 142 is coupled a drive coupling 150 that is configured for coupling to the rotating motor shaft of a motor drive unit (not shown) in hand piece 104. More in particular, the rotatable cutting member 110 is fabricated of a ceramic material with multiple cutting edges. The cutting member 110 has sharp cutting edges 152a and 152b on opposing sides of window 155 therein which rotate in the lateral opening or window 156 of the outer sleeve 140 for cutting soft tissue. The ceramic cutting member 110 additionally has sharp burr edges 160 at its distal end. The burr edges 160 can range in number from 2 to 10 or more and in the variation of FIG. 2A has three such burr edges. The burr edges 160 wrap around the distalmost end 162 the cutting member wherein such burr end edge portions 164 can be use for cutting or drilling in bone. The motor drive is adapted to rotate the cutting member 110 at speeds ranging from 1,000 rpm to 20,000 rpm. The cutting member 110 rotates and shears tissue in the opening or window 156 in the outer sleeve 140 which is configured with multiple teeth 165 which can assist in engaging and shearing tissue.

Now referring to FIG. 2B, it can be seen that cutting member 110 also carries an active RF electrode 115 in a surface opposing the window 155 in the cutting member 110. The electrode 115 is provided in a recess between two of the burr edges 160. The active electrode 115 is configured with a plurality of jagged edges 166 which allow for focusing of RF current in a saline working space to facilitate plasma ignition. The return electrode 120 can consist of the outer surface of the metal outer sleeve 140. The active electrode 115 also has at least one opening 170 therein which communicates with the fluid extraction passageway 172 (FIG. 1) in the sleeve 142. As also can be seen in FIG. 2B, one or more aspiration ports 174 are shown in the surface of the ceramic cutting member 110 which allows for fluid outflows in response to the negative pressure source 175 (FIG. 1) when the cutting member 110 is in the window-closed position.

As can be understood from FIG. 1, the probe 105 is detachably coupled to the hand piece 104 in a first orientation with the window 156 of the outer sleeve 140 in an upward orientation but it could also be coupled to the hand piece in a downward orientation which is rotated 180°. It can be understood that various orientations are necessary to orient the working end 108 either upward or downward relative to the hand piece 104 to allow the physician to interface the cutting member 110 with targeted tissue in all directions without having to manipulate the hand piece in 180° to access tissue.

FIG. 1 further shows that the system 100 also includes a negative pressure source 175 coupled to aspiration tubing 176 which communicates with a flow or extraction channel extending through the hand piece 104 to aspirate fluid and resected tissue chips through a fluid extraction passageway 172 in the inner sleeve 142. In FIG. 1, it also can be seen that the system 100 includes an RF source 180 and controller 185 that are operatively connected to the electrode arrangement. The controller 185 and microprocessor therein together with control algorithms are provided to operate and control all functionality, which includes controlling the motor drive to move a motor-driven component of the probe working end 108 as well as for controlling the RF source 180 and the negative pressure source 175 which can aspirate fluid and tissue chips to a collection reservoir.

Figure 3B:
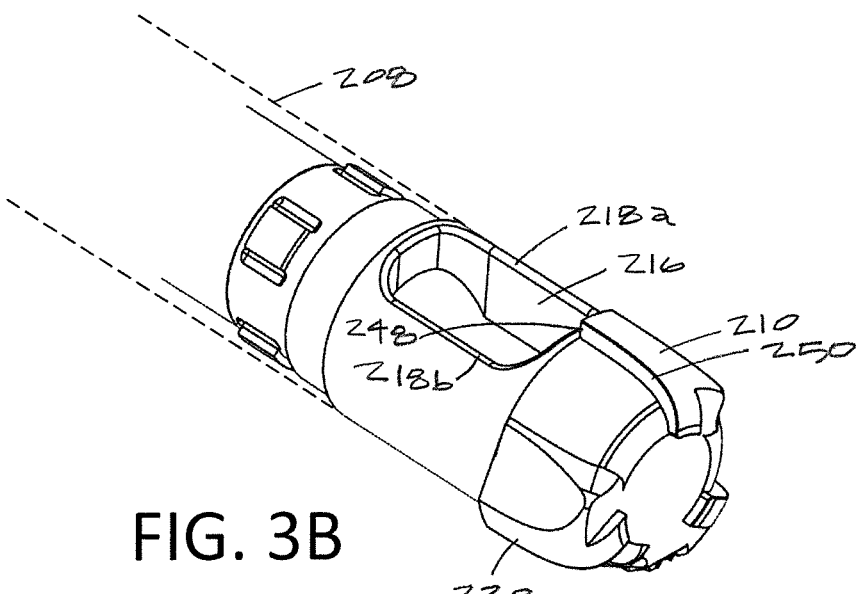
FIG. 3B is a view of the ceramic cutting member of FIG. 3B rotated 180° and separated from the outer sleeve showing an inner sleeve cutting window.
Figure 3A:
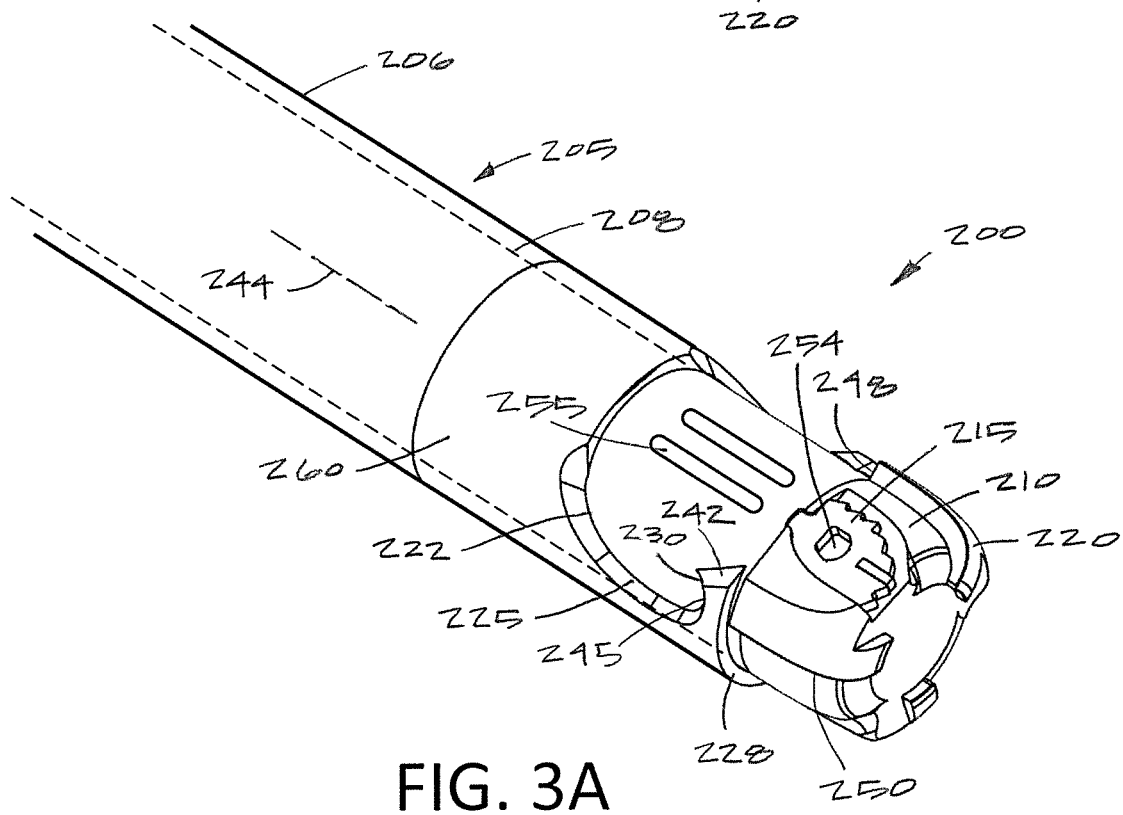
FIG. 3A is a perspective view of a variation of a working end similar to that of FIGS. 2A-2B, wherein the working end includes an outer sleeve window with a barb-like features for capturing and retaining tissue to be sheared by the ceramic cutting member.
Figure 3C:
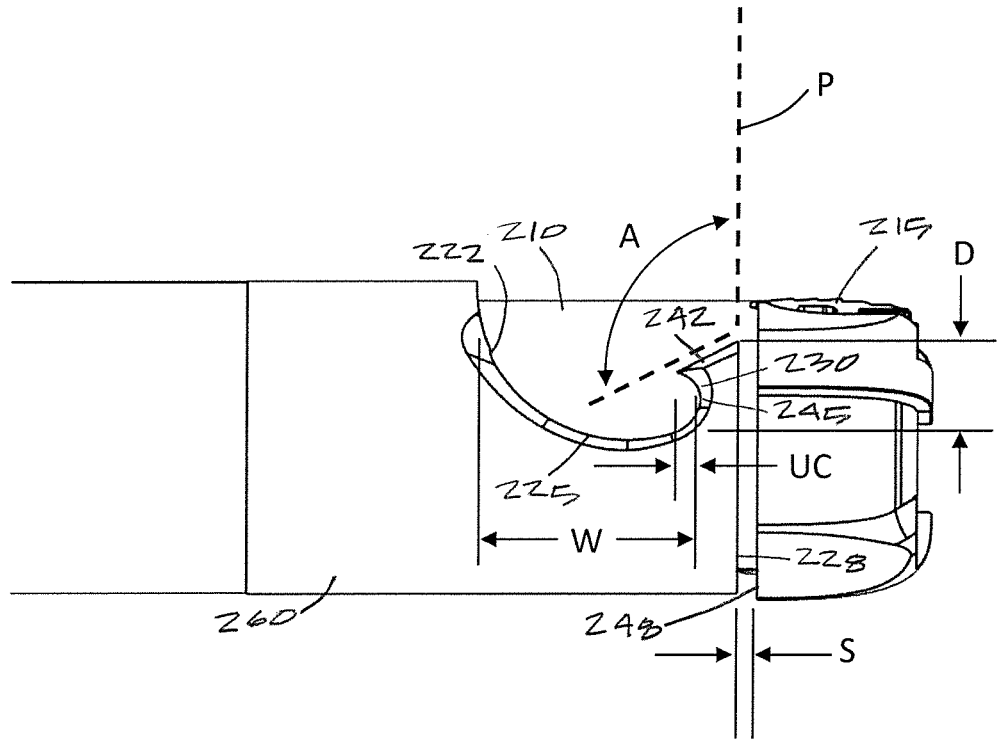
FIG. 3C is a side perspective view of a working end of FIG. 3A showing various features of the methods of the outer sleeve window.
Figure 4:
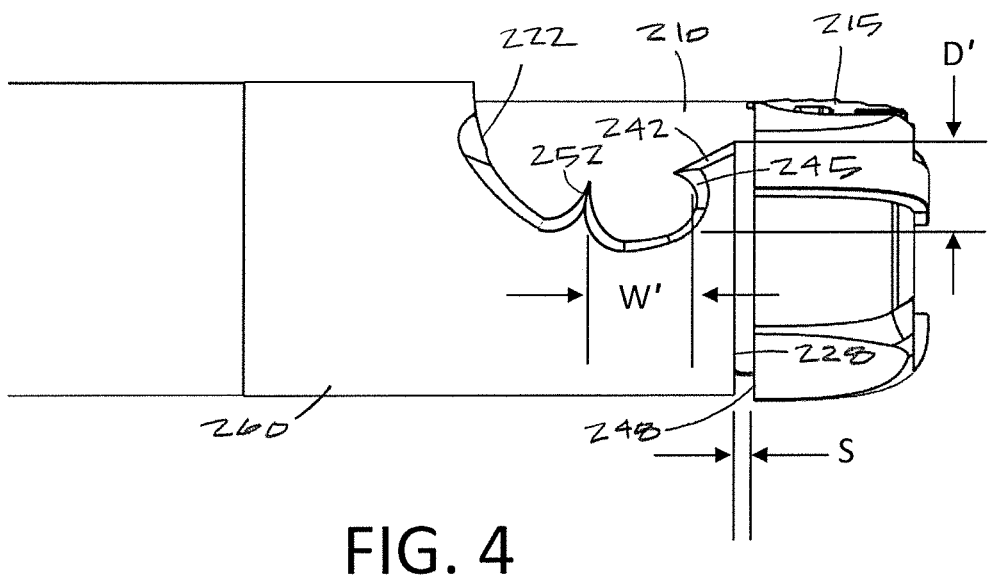
FIG. 4 is a side view a working end similar to that of FIG. 3C with a different configuration of outer sleeve window.

FIG. 3A illustrates another variation of working end 200 of shaft assembly 205 with outer sleeve 206 and inner sleeve 208 that is very similar to that of FIGS. 1, 2A-2B. In FIG. 3A, it can be seen that the ceramic cutting member 210 is adapted to rotate in the working end 200. In this variation, the cutting member 210 carries a differently shaped active electrode 215. FIG. 3B shows the ceramic 210 separated from the outer sleeve 206 and rotated 180° to show the cutting window 216 and sharp edges 218a and 218b located proximal to the distal burr portion 220 which is similar to that of FIG. 2A. Further, FIGS. 3A and 3C show that the outer sleeve 206 has an opening or window 222 with a single scalloped lateral side 225 that differs from the previous embodiment which had a plurality of teeth 165 (FIG. 2A). In this variation, the distal end surface 228 of the outer sleeve 206 transitions into the scalloped side 225 of the window 222 with a barb-like portion 230 that is adapted to prevent string-like, sinewy soft tissue from being wrapped in 360° around the cutting member 210. Referring to FIGS. 3A and 3C, the barb-like portion 230 includes an angled surface 242 that is angled relative to a plane P that is transverse to the axis 244 of the shaft assembly 205 (FIGS. 3A, 3C). Further, the barb-like portion 230 as an undercut edge 245 that can capture and retain such sinewy tissue so that does it does not escape the window 222 to become wrapped around cutting member 210 in space S between the distal end surface 228 of the outer sleeve 206 in the proximal faces 248 of the burr edges 250. The angle A of the angled surface 242 relative to plane P can range from 10° to 60°. Further, the space S with between the distal surface 228 of the sleeve 206 and the proximal faces 248 of the burr edges 250 is less than 0.050" or less than 0.020" (FIG. 3C). In another aspect, the barb-like features or portions 230 of the window 222 have an area proximal to the barb feature 230 that has a depth D, width W and undercut UC that can accommodate and direct the sinewy tissue into a location for shearing by sharp edges 218a-218b of the cutting window 216. The outer sleeve window 222 has a depth D that is at least 2 mm or at least 3 mm. The width W is at least 2 mm, at least 3 mm or at least 4 mm. The undercut UC is at least 0.5 mm or at least 1 mm 1 mm (FIG. 3C). FIG. 4 shows another variation of window 222 which has width W' and a depth D' that have the above minimum dimensions with at least one additional tooth 252 in the window.

Referring to FIG. 3A, the ceramic cutting member 210 again has an aspiration port 254 in the electrode 215 as well as aspiration ports 255 in the cutting member that communicate with a aspiration channel in the cutter and probe. In use, RF current delivery flows between the active electrode 215 and the return electrode 260 and is adapted to ignite plasma around the active electrode 215. It can be understood that when electrode arrangement is energized while submerged in a conductive fluid (e.g., saline), a plasma will be ignited about the active electrode 215 which can electrosurgically ablate tissue.

Now turning to FIGS. 5A-5D, illustrations are provided to show several steps of a method of the invention in performing a subacromial decompression procedure with the single probe of FIGS. 3A-3C without the need for tool exchange. In the schematic view of FIG. 5A, it can be seen that the patient's shoulder joint 400 has a bony protrusion or spur 402 on the acromuim 404 that is impinging on bursa 410 in the joint which can cause significant pain during movement.

Figure 5A:
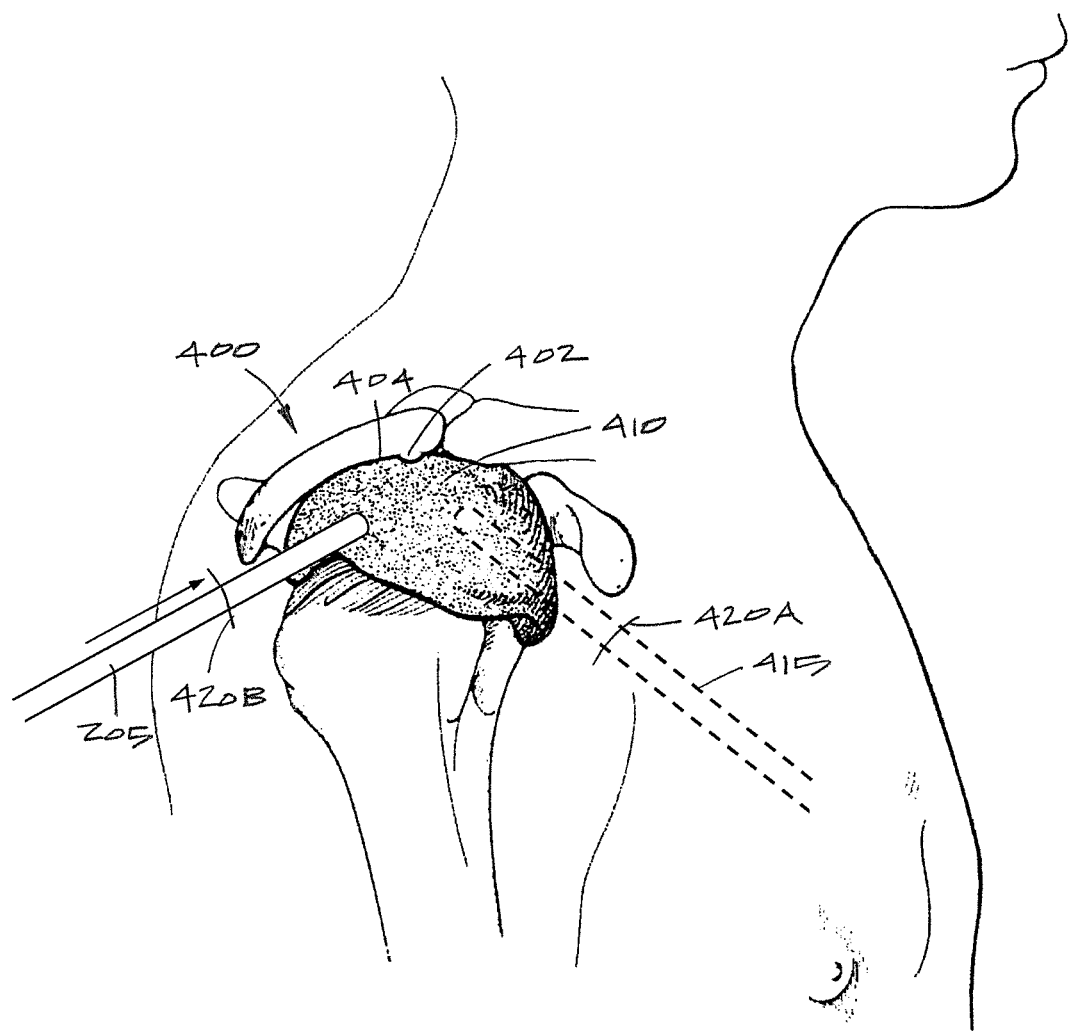
FIG. 5A is an illustration of an initial step of a method of the invention in performing a subacromial decompression procedure wherein an endoscope access is provided followed by a tool access for introducing the probe of FIG. 3A into the patient's shoulder joint.

FIG. 5A depicts a endoscope 415 in phantom view being introduced into the shoulder joint through a first access or portal 420A. FIG. 5A further shows a probe shaft assembly 205 being introduced through a second access or portal 420B wherein the probe shaft assembly 205 and working end 200 are of the type shown in FIG. 3A.

Figure 5B:
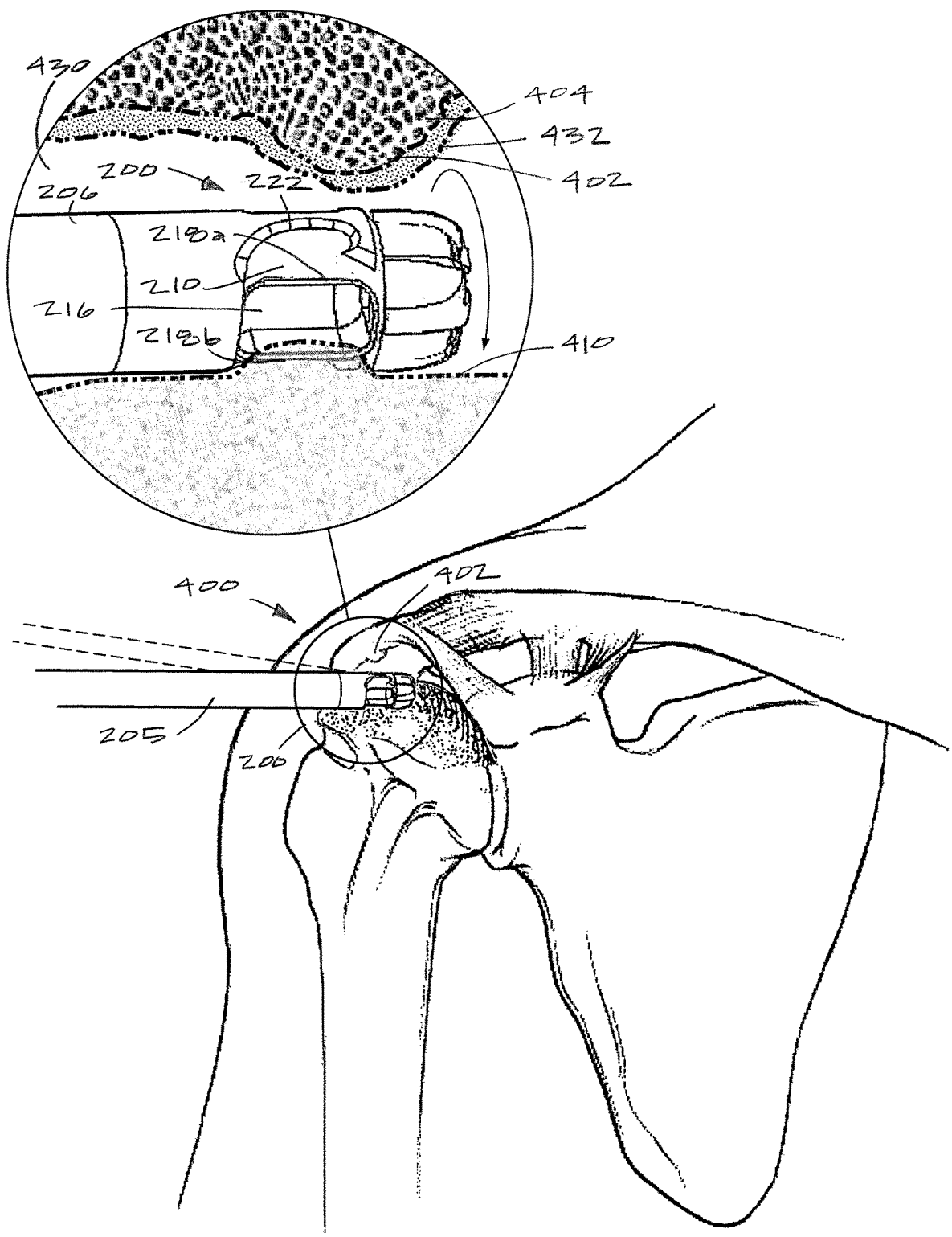
FIG. 5B illustrates a subsequent step of performing the subacromial decompression procedure where the cutting window of the ceramic cutter of FIG. 3A is shown rotating at high speed to cut soft tissue or bursa to expand a treatment space.

FIG. 5B is a schematic view of the shoulder from a different angle illustrating a subsequent step of performing the subacromial decompression procedure. The working end 200 of the probe of FIG. 3A is shown in the subacromial space 430 where the ceramic cutter 210 is rotated or oscillated at high speed and the sharp edges 218a and 218b of the cutter window 216 cut soft tissue or bursa 410 in outer sleeve window 222 to expand the fluid-filled subacromial or treatment space 430.

Figure 5C:
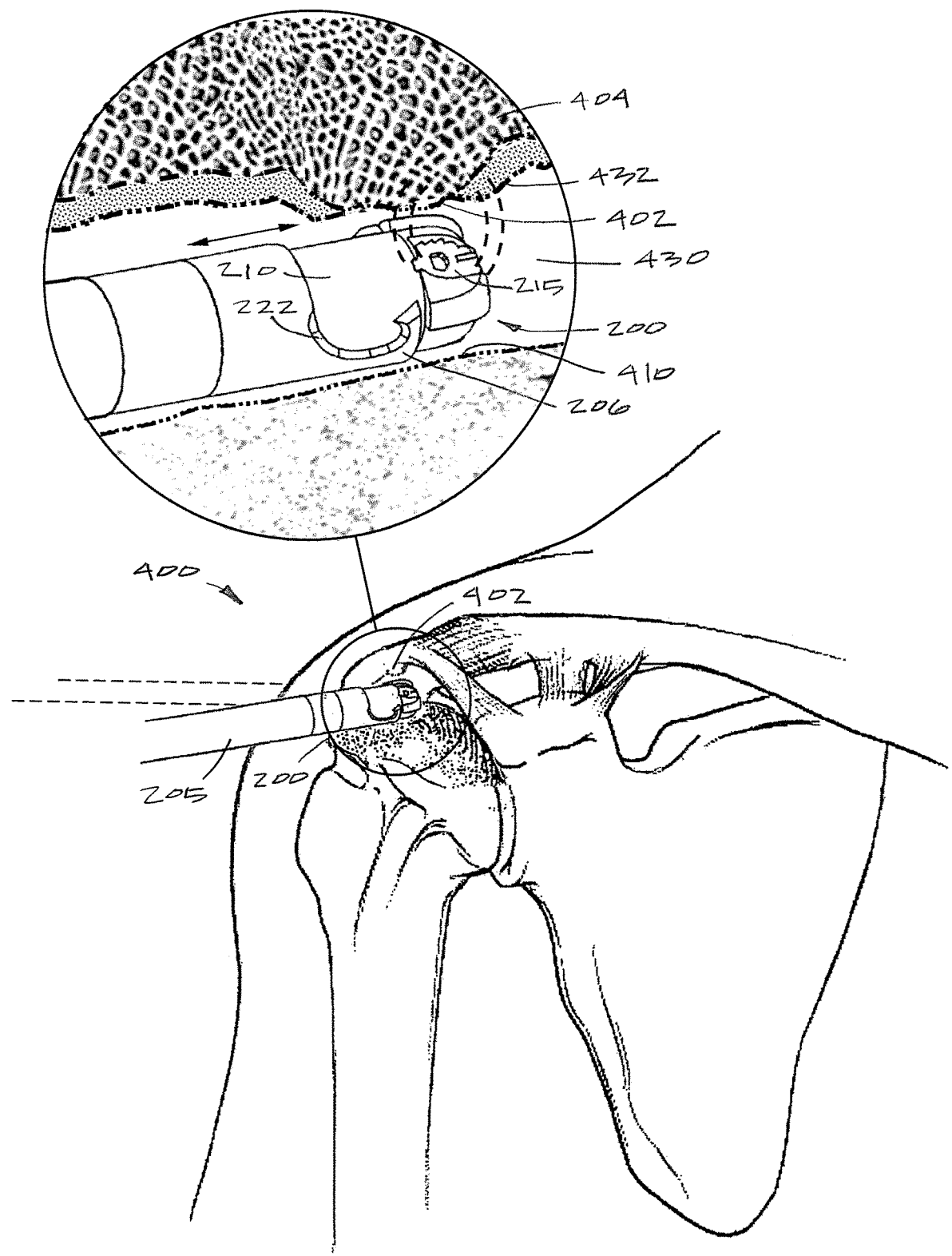
FIG. 5C illustrates a subsequent step of the subacromial decompression procedure where the ceramic cutter of FIG. 3A is stopped from rotation and the RF electrode is exposed and energized to ablate soft tissue overlying a bony protrusion or bone spur.

FIG. 5C illustrates a subsequent step of the procedure where the ceramic cutter 210 of FIG. 3A is stopped from rotation in a position where the RF electrode 215 is exposed in window 224 of outer sleeve 206. Thereafter, the electrode 215 is energized to create a plasma which is used to ablate soft tissue overlying the bony protrusion 402, for example, the coracoacromial ligament 432.

Figure 5D:
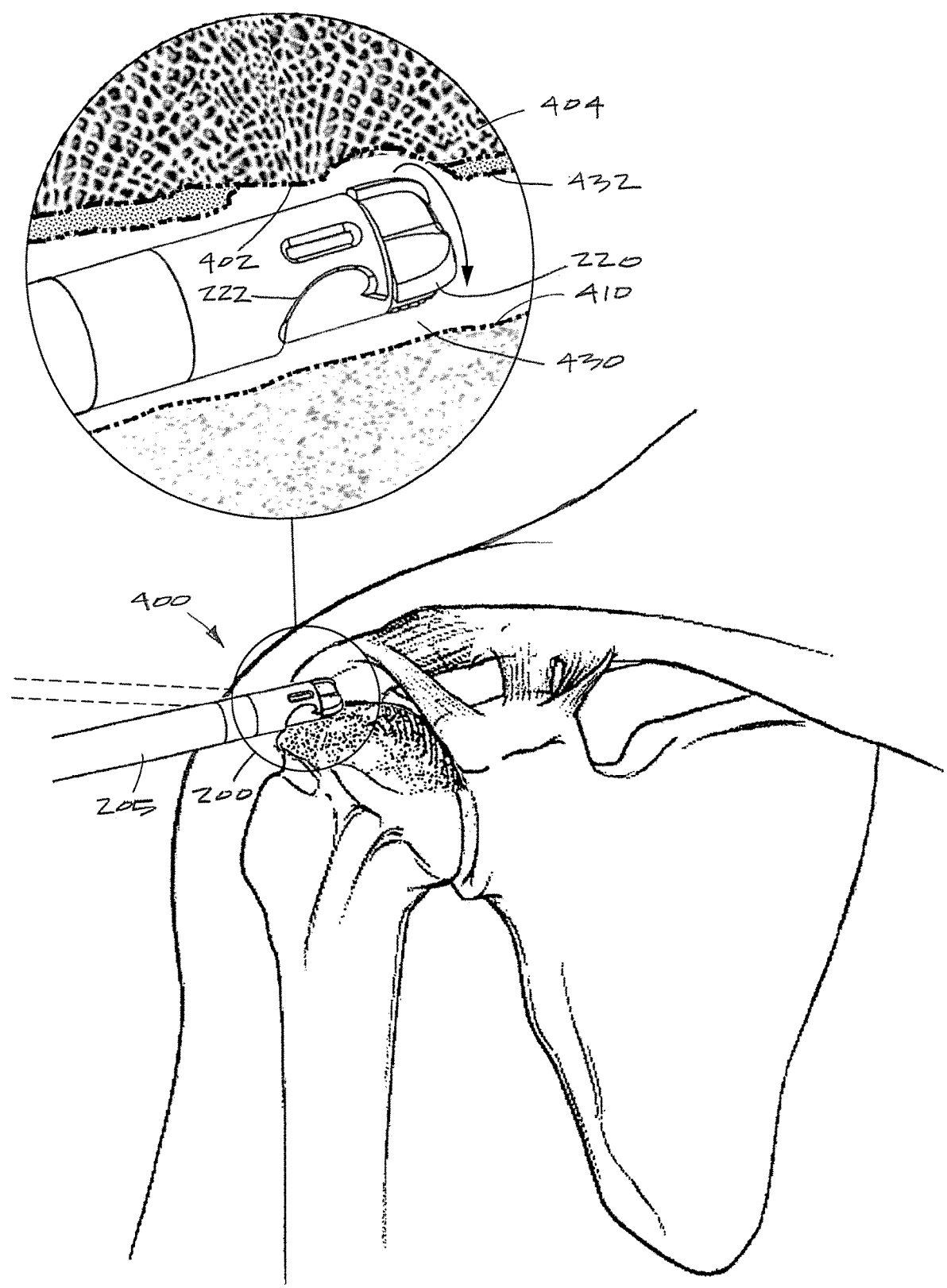
FIG. 5D illustrated another step of the method wherein the burr portion of the ceramic cutter is rotated at high-speed to cut away the bony protrusion of FIG. 5C.

FIG. 5D then illustrates a final step the subacromial decompression method wherein the burr portion 220 of the ceramic cutter 210 is rotated at high-speed to cut away the bony protrusion 402 from the acromuim 404. It can be appreciated that the various steps of the procedure which require different treatment tools can be accomplished with a single probe of FIG. 3A without it being necessary the withdraw the probe from the patient's shoulder. Whenever tool exchange is necessary, as in the prior art, it can be exceedingly difficult to navigate back to the exact location needed to treat the target tissue. Thus, the use of a single probe with multiple functional elements can save a significant amount of time and provide for safer procedure.

In general, referring to FIGS. 5A-5D, a method of arthroscopic subacromial decompression, comprises: forming a first portal 420A in a patient shoulder for introduction of an endoscope to visualize the subacromial space, forming a second portal 420B for introduction of a probe for modifying tissue in the subacromial space 430, introducing a working end 200 of the probe through the second portal into the subacromial space 430, wherein the working end 200 includes a first element for cutting soft tissue, a second element for applying RF energy to tissue, and third element for bone burring. Thereafter, the physician cuts bursa with the first element, apply RF energy to ablate bone surface tissue with the second element, and burr bone with the third element to thereby decompress the subacromial space 430.

In this method of subacromial decompression, the cutting step is accomplished with a first element that comprises a motor-driven windowed cutting portion of a ceramic cutter 210. This cutting step includes extracting cut soft tissue and bursa through an extraction channel in the ceramic cutter and probe that is coupled to the negative pressure source 275. The method further includes applying RF energy with the second element that comprises a bipolar RF electrode arrangement carried by the working end 200. In this method, the burring bone step is accomplished with a third that comprises a motor-driven burr portion 220 of the ceramic cutting member 210 (FIG. 3A). The method further comprising the step of introducing saline into the subacromial space to open the space and facilitate plasma formation with the RF electrode arrangement.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of shoulder arthroscopy, comprising:
   forming a first portal in a shoulder of a patient to access a subacromial space in the shoulder;
   introducing an endoscope through the first portal to visualize the subacromial space;
   forming a second portal in the shoulder to access the subacromial space;

introducing a working end of a probe having a longitudinal axis through the second portal into the subacromial space, wherein the working end includes a first element for cutting soft tissue, a second element for applying RF energy to tissue, and a third element for bone cutting or burring;

cutting soft tissue with the first element to access targeted bone, wherein the first element includes a windowed cutting member, and wherein said cutting soft tissue with the first element includes rotating the windowed cutting member in a window of an outer sleeve, the window of the outer sleeve including a single scalloped lateral side, the outer sleeve including a distal end surface that transitions into the single scalloped lateral side with a first barb-like portion for capturing and retaining tissue within said outer sleeve window, wherein the single scalloped lateral side extends in a proximal direction along the outer sleeve from the first barb-like portion to a proximal end of the single scalloped lateral side, the proximal end of the single scalloped lateral side being void of a barb-like portion such that the first barb-like portion is the only barb-like portion positioned along the single scalloped lateral side;

applying radiofrequency (RF) energy to ablate bone surface tissue with the second element; and burring the targeted bone with the third element to thereby treat the subacromial space.

2. The method of shoulder arthroscopy of claim 1, wherein at least two of the cutting, the applying RF energy, and the burring steps are performed successively without removing the working end of the probe from the second portal.

3. The method of shoulder arthroscopy of claim 1, wherein all three of the cutting, the applying RF energy, and the burring steps are performed successively without removing the working end of the probe from the second portal.

4. The method of shoulder arthroscopy of claim 1, wherein said cutting soft tissue with the first element comprises rotating the windowed cutting member with a motor in a hand piece attached to the probe.

5. The method of shoulder arthroscopy of claim 4, wherein the third element comprises a burr-edged portion of the working end, wherein the burring step comprises rotating the burr-edged portion of the working end with the motor.

6. The method of a shoulder arthroscopy of claim 5, wherein the burr-edged portion is distal to the windowed cutting member.

7. The method of shoulder arthroscopy of claim 1 further comprising the step of introducing a fluid into the subacromial space.

8. The method of shoulder arthroscopy of claim 1, wherein the first barb-like portion includes an angled surface that extends back in a proximal direction from the distal end surface of the outer sleeve and that, while extending back in this way, angles toward the longitudinal axis of the probe until terminating in a pointed barb tip at a proximal end of the angled surface, wherein the first barb-like portion is undercut under the pointed barb tip so as to include an undercut edge that is positioned distally of the pointed barb tip along the outer sleeve to thereby form part of the single scalloped lateral side of the window of the outer sleeve.

9. The method of shoulder arthroscopy of claim 8, wherein a distance from the proximal end of the single scalloped lateral side to a distalmost part of the undercut edge measures at least 3 mm.

10. The method of shoulder arthroscopy of claim 9, wherein a distance from the proximal end of the single scalloped lateral side to a distalmost part of the undercut edge measures between 2 mm and 4 mm.

11. A method of shoulder arthroscopy, comprising:

providing an arthroscopic probe having a longitudinal axis and including a working end configured with a first element for cutting soft tissue, a second element for applying RF energy to tissue, and a third element for bone cutting or burring;

introducing the working end of the arthroscopic probe into a subacromial space in a shoulder of a patient; and removing tissue from the subacromial space by successively performing each of the following steps in any order: (i) cutting soft tissue with the first element, (ii) applying RF energy to tissue with the second element, and (iii) cutting or burring bone with the third element, wherein said steps are performed without withdrawing the working end from the subacromial space between at least some of the successive steps, wherein the first element includes a windowed cutting member, and wherein said cutting soft tissue with the first element includes rotating the windowed cutting member in a window of an outer sleeve, the window of the outer sleeve including a single scalloped lateral side, the outer sleeve including a distal end surface that transitions into the single scalloped lateral side with a first barb-like portion for capturing and retaining tissue within said outer sleeve window, wherein the single scalloped lateral side extends in a proximal direction along the outer sleeve from the first barb-like portion to a proximal end of the single scalloped lateral side, the proximal end of the single scalloped lateral side being void of a barb-like portion such that the first barb-like portion is the only barb-like portion positioned along the single scalloped lateral side, wherein the first barb-like portion includes an angled surface that extends back in a proximal direction from the distal end surface of the outer sleeve and that, while extending back in this way, angles toward the longitudinal axis of the probe until terminating in a pointed barb tip at a proximal end of the angled surface, wherein the first barb-like portion is undercut under the pointed barb tip so as to include an undercut edge that is positioned distally of the pointed barb tip along the outer sleeve to thereby form part of the single scalloped lateral side of the window of the outer sleeve.

12. The method of shoulder arthroscopy of claim 11, wherein the soft tissue includes bursa.

13. The method of shoulder arthroscopy of claim 11, wherein the applying RF energy step ablates tissue around a bone surface in the subacromial space targeted for bone cutting or burring.

14. The method of shoulder arthroscopy of claim 11, wherein the applying RF energy step treats a coracoacromial ligament.

15. The method of shoulder arthroscopy of claim 11, wherein the applying RF energy step coagulates blood vessels.

16. The method of shoulder arthroscopy of claim 11, wherein the cutting or burring bone step removes bone from an acromion.

17. The method of shoulder arthroscopy of claim 11 further comprising the step of visualizing the subacromial space with an endoscope while performing the removing step.

18. The method of shoulder arthroscopy of claim 11 further comprising a step of introducing a fluid into the subacromial space.

19. A method of arthroscopic treatment, comprising:
providing an arthroscopic probe having a longitudinal axis and including a working end configured with a first element for cutting soft tissue, a second element for applying RF energy to tissue and a third element for bone cutting or burring;
introducing the working end of the arthroscopic probe into a site in a joint of a patient; and
treating the joint by performing each of the following steps in any order: (i) cutting soft tissue with the first element, (ii) applying RF energy to ablate tissue with the second element, and (iii) burring or cutting bone with the third element, wherein said steps are performed without withdrawing the working end from the site between at least some of the successive steps,
wherein the first element includes a windowed cutting member, and wherein said cutting soft tissue with the first element includes rotating the windowed cutting member in a window of an outer sleeve, the window of the outer sleeve including a single scalloped lateral side, the outer sleeve including a distal end surface that transitions into the single scalloped lateral side with a first barb-like portion for capturing and retaining tissue within said outer sleeve window, wherein the single scalloped lateral side extends in a proximal direction along the outer sleeve from the first barb-like portion to a proximal end of the single scalloped lateral side, the proximal end of the single scalloped lateral side being void of a barb-like portion such that the first barb-like portion is the only barb-like portion positioned along the single scalloped lateral side, wherein the first barb-like portion includes an angled surface that extends back in a proximal direction from the distal end surface of the outer sleeve and that, while extending back in this way, angles toward the longitudinal axis of the probe until terminating in a pointed barb tip at a proximal end of the angled surface, wherein the first barb-like portion is undercut under the pointed barb tip so as to include an undercut edge that is positioned distally of the pointed barb tip along the outer sleeve to thereby form part of the single scalloped lateral side of the window of the outer sleeve.

20. The method of arthroscopic treatment of claim 19, wherein the third element comprises a burr-edged portion of the working end, wherein the burring step comprises rotating the burr-edged portion of the working end with a motor in a hand piece attached to the probe, wherein the burr-edged portion is distal to the windowed cutting member.

21. The method of arthroscopic treatment of claim 20, wherein the site is in a shoulder of a patient.

22. The method of arthroscopic treatment of claim 21, wherein the arthroscopic treatment comprises a subacromial decompression procedure.

23. The method of arthroscopic treatment of claim 20, wherein the site is in a knee of a patient.

24. The method of arthroscopic treatment of claim 23, wherein the arthroscopic treatment comprises a ligament repair procedure.

25. The method of arthroscopic treatment of claim 19, wherein the site is in a hip of a patient.

26. The method of arthroscopic treatment of claim 25, wherein the arthroscopic treatment comprises a femoroacetabular impingement procedure.

27. The method of arthroscopic treatment of claim 19, wherein the first element and the second element are disposed on a first side of the working end, wherein the cutting soft tissue and the applying RF steps are performed by a user without the user changing grip and/or rotating a hand piece attached to the arthroscopic probe about its longitudinal axis.

\* \* \* \* \*